United States Patent [19]

Jensen

[11] 4,366,384
[45] Dec. 28, 1982

[54] AIR BUBBLE DETECTOR

[75] Inventor: Lynn E. Jensen, Clearfield, Utah

[73] Assignee: Cutter Laboratories, Inc., Berkeley, Calif.

[21] Appl. No.: 160,664

[22] Filed: Jun. 18, 1980

[51] Int. Cl.³ .............................................. G01N 15/06
[52] U.S. Cl. ..................................... 250/575; 250/577
[58] Field of Search ............... 250/574, 575, 577, 209, 250/210; 356/134; 73/293

[56] References Cited

U.S. PATENT DOCUMENTS

| | | | |
|---|---|---|---|
| 3,618,061 | 11/1971 | Livers | 250/577 |
| 3,636,360 | 1/1972 | Oishi et al. | 356/134 |
| 3,900,396 | 8/1975 | Lamadrid | 250/575 |
| 3,908,441 | 9/1975 | Virloget | 73/293 |
| 4,123,227 | 10/1978 | Heim et al. | 250/577 |

Primary Examiner—David C. Nelms
Attorney, Agent, or Firm—Weissenberger & Peterson

[57] ABSTRACT

Air bubbles in a transparent intravenous solution conduit are detected, regardless of whether the solution is opaque or clear, by directing a light source at the conduit and detecting light shining through the solution with a first light sensor while detecting light reflected from the interior wall of the conduit with a second light sensor. If liquid is present in the conduit, whether clear or opaque, one sensor will see a low light level while the other sees a high level. If air is present, both sensors see a high light level. By EXCLUSIVE-OR'ing the outputs of the two sensors, a logic signal is obtained which is high only when the presence of liquid in the conduit is being detected. Means using two sensor assemblies spaced axially along the conduit, and a counter associated with each, are also provided to allow passage of minor air bubbles, and to provide a backup signal representative of a predetermined volume of air passing either assembly independently of the other.

10 Claims, 7 Drawing Figures

|  | DIRECT SENSOR | REFLECT SENSOR |
|---|---|---|
| CLEAR LIQUID | LIGHT | DARK |
| OPAQUE LIQUID | DARK | LIGHT |
| AIR | LIGHT | LIGHT |
| NO LIGHT | DARK | DARK |
FIG. 3a
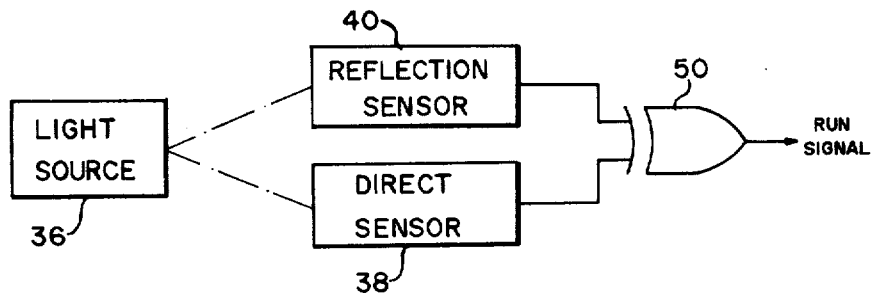
FIG. 4
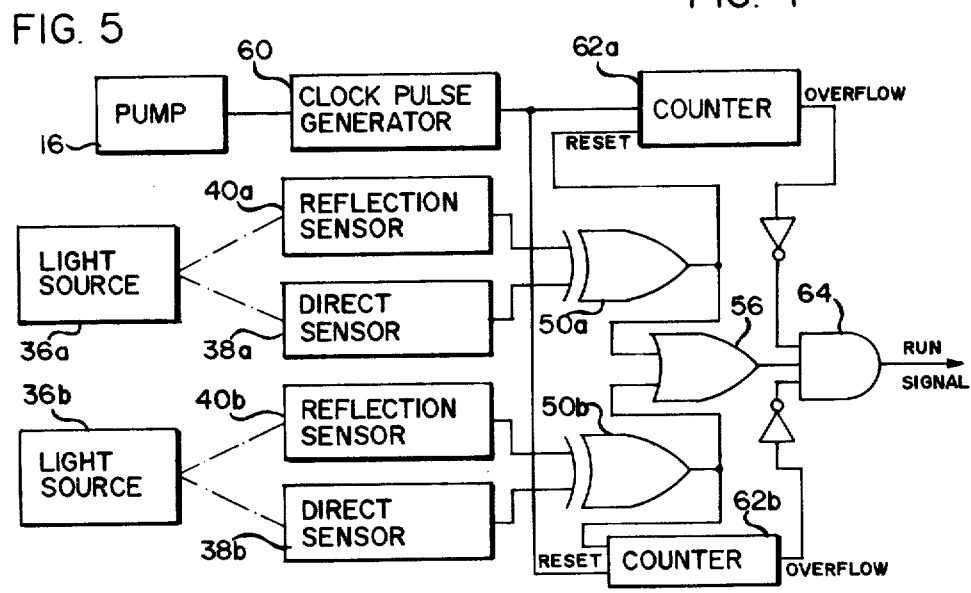
FIG. 5 ated to a patient. The device is typically used as a safety feature in electrically driven precision pumps which pump precisely measured amounts of intravenous solution into the patient's bloodstream. This solution is typically conveyed through a transparent disposable plastic conduit which has a generally circular cross section. The solution involved may be of several types: a clear liquid such as the conventional dextrose solution used for intravenous feeding; an opaque milky liquid such as Intralipid ®; or blood.

AIR BUBBLE DETECTOR

BACKGROUND OF THE INVENTION

This invention relates to a device for detecting air bubbles in an intravenous solution being administered to a patient. The device is typically used as a safety feature in electrically driven precision pumps which pump precisely measured amounts of intravenous solution into the patient's bloodstream. This solution is typically conveyed through a transparent disposable plastic conduit which has a generally circular cross section. The solution involved may be of several types: a clear liquid such as the conventional dextrose solution used for intravenous feeding; an opaque milky liquid such as Intralipid ®; or blood.

Methods for detecting air bubbles in such solutions by photoelectric means are well-known. They generally rely on a difference in the amount of light transmitted through the liquid and through air. Devices of this type, however, are inherently unsuitable for indiscriminate use with various kinds of intravenously administered solutions without appropriate adjustment.

To overcome this problem, devices have been marketed in which the light beam of the photoelectric bubble detector is directed not through the axis of the conduit, but through the wall of the conduit generally tangentially to its inner diameter. The difference in the reflective characteristics of the inner wall of the tube when liquid is present as opposed to the absence of liquid is detected by a light sensor and used to produce an appropriate signal indicating the presence of air. Unfortunately, the last-named method requires the use of a conduit whose translucence and dimensions must be controlled within tolerances so strict as to be economically undesirable for disposable equipment. In addition, the need for maintaining close tolerances in equipment of this type increases the chances of malfunction due to careless positioning of the conduit by the operator.

SUMMARY OF THE INVENTION

In accordance with the invention, it has been found that the disadvantages of prior art devices can be overcome by using a pair of light sensors and positioning one of them adjacent the conduit at a position more or less diametrically opposite from the light source, while the other is positioned adjacent the circumference of the conduit generally halfway between the light source and the first-mentioned light sensor. The outputs of the two light sensors are fed into a logic circuit which produces one output when the light levels seen by the two sensors are generally alike, and another when they are substantially different.

Due to the interrelationship between the reflective parameters of the inner wall of the conduit and the nature of the fluid present in the conduit, a truth table can be established which has separate and distinct logic relationships for air, clean solution, opaque solution (including blood), and light source failure. It is thus possible for the logic circuit to provide a simple, unambiguous signal when intravenous solution free of air bubbles is being detected in the conduit, regardless of which kind of solution is being administered.

In accordance with a further aspect of the invention, a pair of detector assemblies may be axially spaced along the conduit, and the logic circuit may be so arranged that it will respond only to the simultaneous presence of air at both detector assemblies. This feature prevents the unnecessary operation of the emergency pump shutoff by air bubbles which are not large enough to injure the patient. When this is done, backup circuitry is preferably provided to operate the shutoff even if one of the detector assemblies malfunctions. In accordance with the invention, the backup circuitry counts the number of pump strokes and triggers the emergency shutoff if air is detected by either one of the detector assemblies for a number of pump strokes greater than that necessary for a predetermined amount of fluid to pass a given point.

BRIEF DESCRIPTION OF THE DRAWINGS

FIG. 3a is the truth table for the operation of the assembly of FIG. 3;

FIG. 4 is a block diagram of the basic logic circuitry of this invention;

FIG. 5 is a block diagram of a more sophisticated embodiment of the invention.

DETAILED DESCRIPTION OF THE INVENTION

Figures 1, 2, 3:
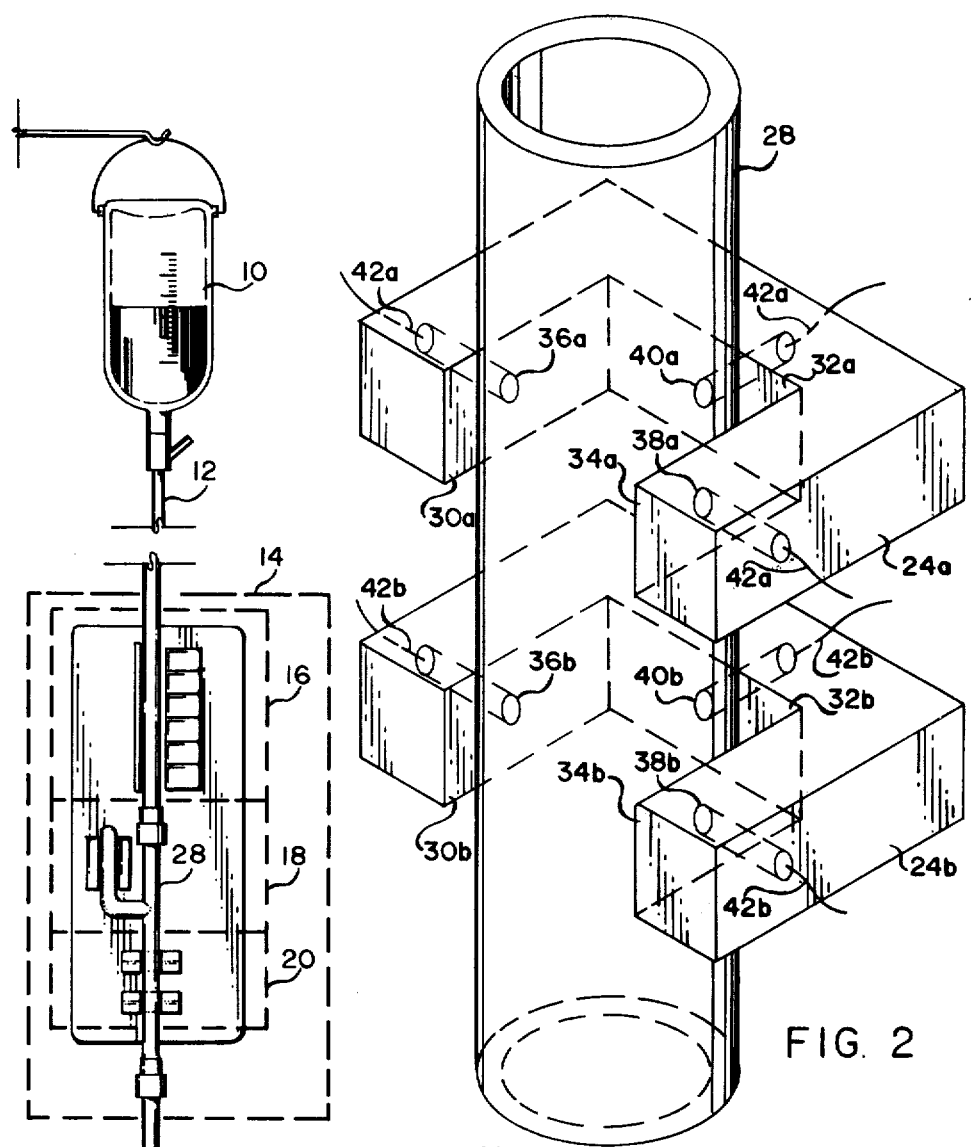
FIG. 1 is a schematic view illustrating a typical environment in which the present invention may be used.
FIG. 2 is a perspective view showing the physical arrangement of the light sensors with respect to the fluid conduit in the device of this invention.
FIG. 3 is a plan view of a detector assembly constructed in accordance with this invention, showing the light paths involved in its operation.

FIG. 1 shows a typical environment in which this invention is useful. Intravenous solution from a sterile bottle 10 is pumped through plastic tubing 12 by a precision pump 14 which may include a pump unit 16, an occlusion sensor 18, and an air bubble detector 20. Both the occlusion detector 18 and the air pump 20 are conventionally electrically connected to the pump unit 16 in such a way as to shut off the pump unit 16 when an occlusion or an air bubble are detected in the conduit 28 through which the intravenous solution is delivered to the patient. The pump unit 16 and occlusion detector 18 may be of any conventional design and will not be further discussed herein.

Turning now to FIG. 2, the air bubble detector of this invention preferably consists of a pair of detector assemblies or heads 24a, 24b axially spaced along a transparent conduit 28 which is connected to form part of the tubing 12. Each of the heads 24 is generally U-shaped and is designed to receive therein the fluid conduit 28 in such a position that the faces 30, 32, 34 are generally tangential to the outer walls of the conduit 28 when the conduit 28 is in place.

Although the material from which the conduit 28 is fabricated is not particularly critical as long as it is reasonably transparent and has reasonably smooth interior and exterior walls, a typical embodiment of the invention may, for example, use a conduit molded from transparent SAN styrene such as that manufactured by Dow Chemical Corporation, and may have approximately a No. 4 finish. The conduit of the preferred embodiment may have an outer diameter of approximately 4.7 mm and an inner diameter of approximately 3.4 mm. Neither the material nor the finish nor the dimensions given in this example are critical to the performance of the invention.

Each of the detector heads 24a, 24b contains a preferably infrared light source 36, a direct sensor 38 positioned generally diametrically opposite the light source 36, and a reflection sensor 40. The direct sensor 38, in the example given, is preferably located so that the direct light path from the light source 36 to it passes slightly inwardly of the axis 39 of the conduit 28. The reflection sensor 40 has been shown as being positioned along the outer circumference of conduit 28 in a position midway between the light source 36 and the direct sensor 38, but this position is not very critical, and the reflection sensor 40 may be positioned anywhere within a fairly wide arc between the light source 36 and the direct sensor 38. The brighter the light source 36, the less critical is the positioning of the sensors 38 and 40. Electrical leads 42 are connected to the light source 36 and sensors 38 and 40 to connect them to the logic circuitry shown in more detail in FIG. 6.

FIG. 3 illustrates the manner in which the truth table of FIG. 3a for the identification of air bubbles in conduit 28 is established. The nature of the fluid in the conduit 28 affects the reflectivity of the inner surface 44 of conduit 28 to a light beam 46 which is scattered along the wall of conduit 28 by the light source 36.

It has been found that in the presence of a clear liquid in conduit 28, the reflectivity of the inner wall 44 of conduit 28 becomes sufficiently low to prevent a significant amount of light from reaching reflection sensor 40. On the other hand, the direct beam travels through the conduit 28 and the clear liquid therein with little distortion, so that direct sensor 38 is strongly illuminated.

When a milky liquid such as Intralipid ® or a dark liquid like blood is present in the conduit 28, the reflectivity of the inner wall 44 is altered to where a substantial amount of light reaches reflection sensor 40. On the other hand, the opacity of the liquid attenuates the light reaching the direct sensor 38.

If air is present in conduit 28, the inner wall 44 remains reflective, but the direct beam from light source 36 also reaches direct sensor 38 without impediment. It is therefore possible to detect the presence of air in conduit 28 by the fact that both the direct sensor and the reflection sensor are at the same high logic level. For this purpose, the light source 36 is so adjusted that both the direct sensor 38 and reflection sensor 40 are driven to saturation when they are at the "light" logic level, yet remain substantially below saturation when they are at the "dark" logic level.

FIG. 4 illustrates, in block diagram form, a typical manner of utilizing the foregoing logic relationships. The output of reflection sensor 40 and direct sensor 38 are applied to the inputs of an EXCLUSIVE-OR gate 50. The output of gate 50 is a "run" signal whose absence (for fail-safe purposes) may, for example, operate a relay (not shown) to shut off the pump 16 of FIG. 1. By the same token, pump unit 16 can thus be shut off in case of a failure of the light source 36, as the "run" signal will also fail when both the reflection sensor 40 and the direct sensor 38 are dark.

FIG. 5 is a block diagram representation of a somewhat more sophisticated system utilizing the principles of the invention. The light sources 36a and 36b of detector heads 24a and 24b individually operate logic circuits similar to that of FIG. 4 and involving reflection sensors 40, direct sensors 38, and EXCLUSIVE-OR gates 50. The outputs of gates 50a and 50b are OR'd at 56 so that shutoff will occur only when air is detected at both heads 24. This prevents the device from being responsive to small air bubbles which are not injurious to the patient's health.

. In the device of FIG. 5, special provisions are made for the continuing safe operation of the device if one of the two detector assemblies 24 or its associated circuitry fails in a "run" mode. A signal derived in any conventional manner from the pump unit 16 and indicative of its speed of operation is used (as by actuating a conventional clock pulse generator 60) in such a way as to produce one clock pulse each time a small predetermined volume of solution is pumped through the conduit 28. The clock pulses are applied to a pair of counters 62. Each counter is reset whenever its associated detector assembly produces a "run" signal. The overflow outputs of the counters 62 are inverted to produce "run" signals which are logically ANDed with the "run" signal from OR function 56 at 64. In this manner, a single head can continue to operate the device, and it will take a predetermined volume of air passing either sensor head as a single bubble to trigger pump shutoff.

Figure 6:
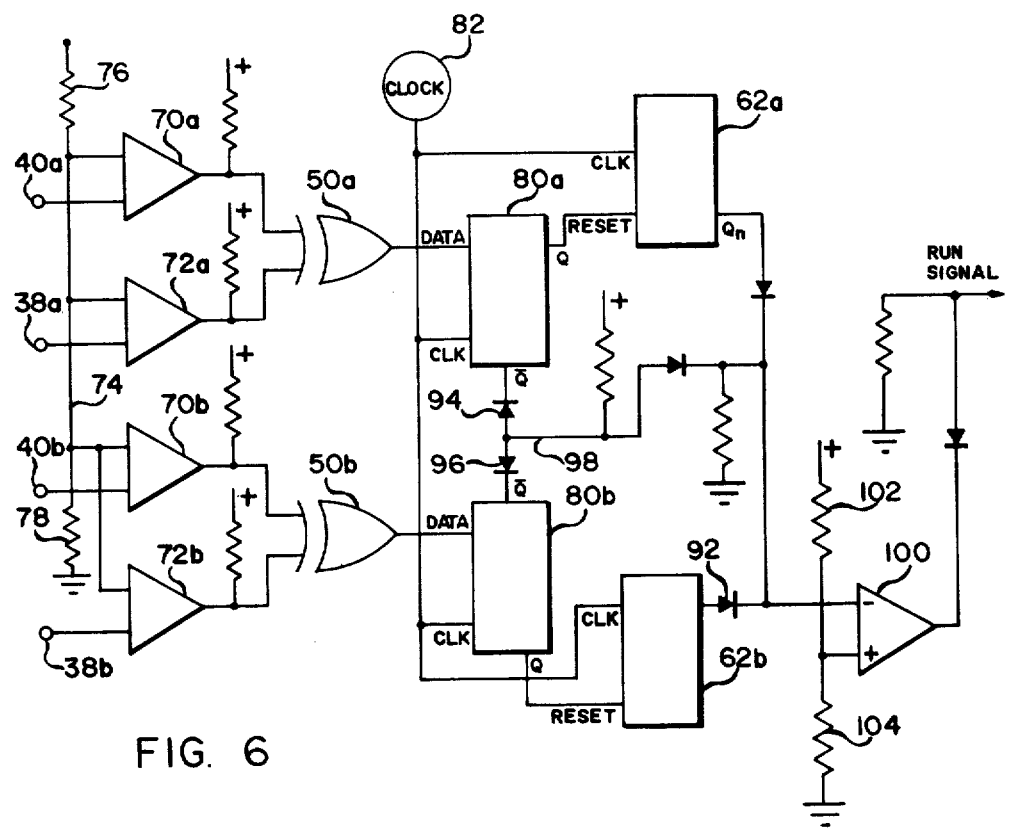
FIG. 6 is a circuit schematic, partly in block form, of a preferred logic circuit used in the embodiment of FIG. 5.

FIG. 6 illustrates a circuit which is well-suited for carrying out the invention. The outputs of sensors 40a and 38a are supplied, respectively, to a pair of comparators 70a, 72a. These comparators compare the level of the outputs of sensors 40a and 38a to a reference level established on line 74 by resistors 76, 78. In like manner, the outputs of sensors 40b and 38b are supplied to the inputs of comparators 70b and 72b. The outputs of comparators 70a and 72a are applied to an EXCLUSIVE-OR gate 50a, which causes the data input of flip-flop 80a to go high whenever liquid is present in conduit 28. In like manner, the outputs of comparator 70b and 72b are applied to EXCLUSIVE-OR gate 50b to make the data input of flip-flop 80b high when the presence of liquid in conduit 28 is being detected.

Clock pulses derived from an appropriate clock pulse generator (not shown in FIG. 6) are applied to clock input 82 preferably at a rate corresponding to the speed of operation of pump unit 16. These clock pulses are applied to the clock inputs of flip-flops 80a and 80b so as to set the outputs of flip-flops 80 and 80b to the data condition present at the trailing edge of the clock pulse.

The clock pulses themselves are counted by backup counters 62a, 62b, which are reset whenever the "Q" outputs of flip-flops 80a and 80b, respectively, are high. When air is present in conduit 28 and flip-flops 80a or 80b (or both) go low at their Q output, the backup counters 62a and/or 62b will count a predetermined number of clock pulses before the overflow output $Q_n$ goes high and triggers a shutoff signal through diode 90 and/or 92.

Although each of the backup counters 62 can trigger the shutoff signal independently, the action of diodes 94, 96 causes line 98 to remain low unless both Q outputs of flip flops 80a and 80b are high. When any shutoff signal trigger condition occurs, a high shutoff signal is applied to the negative input of comparator 100, whose positive input is held at a reference potential determined by resistors 102, 104. The comparator 100 acts as an inverter-driver which, for fail-safe purposes, provides a "run" signal which is low when air is present and high when the system is functioning normally.

Inasmuch as a stopping of the pump unit 16 prevents any further clock pulses from occurring, the system shown in FIG. 6 will freeze in a shut-off condition which must be manually overridden to restart the pump unit 16. Alternatively, the falling edge of the "run" signal can be inverted and applied, with a short delay, to the set inputs (not shown) of flip-flops 80a, 80b to reset the circuit to the "run" condition after the pump shut-off relay has operated in a conventional manner.

I claim:

1. An air detector for use in conjunction with a generally transparent intravenous fluid conduit, the inner wall of said conduit being reflective to light, comprising:
    (a) a light source positioned alongside said conduit;
    (b) first light-detecting means positioned alongside said conduit at a location diametrically opposite and facing said light source, and adapted for receiving direct light passing through the fluid in said conduit;
    (c) second light-detecting means positioned alongside said conduit between said light source and said first light-detecting means, and adapted for receiving reflections from said inner wall of the conduit; and
    (d) logic means coupled to said first and second light-detecting means and arranged to produce a particular signal when, and only when, the light levels detected separately and simultaneously by said first and second light-detecting means bear a predetermined logical relationship to one another.

2. The detector of claim 1, wherein said logical relationship is that in which one of said light-detecting means detects a high level of light, and the other detects a low level of light.

3. In association with a generally cylindrical transparent intravenous fluid conduit, the inner wall of said conduit being reflective to light, an air detector comprising:
    (a) a pair of detector units spaced from one another in the direction of the axis of said conduit, each said detector unit including
        (i) a light course positioned alongside said conduit
        (ii) first light-detecting means positioned alongside said conduit at a location generally diametrically opposite and facing said light source and adapted for receiving direct light passing through said conduit; and
        (iii) second light-detecting means positioned alongside said conduit between said light source and said first light-detecting means and adapted for receiving reflections from said inner wall of said conduit; and
    (b) logic means coupled to said first and second light-detecting means of each of said detector units and arranged to produce a particular signal when, and only when, in each of said detector units, the light levels detected separately and simultaneously by said first and second light-detecting means bear a predetermined logical relationship to one another.

4. An air detector for use in conjunction with a generally transparent fluid conduit, the inner wall of said conduit being reflective to light, comprising:
    (a) a light source;
    (b) first light-detecting means so positioned as to detect light traveling from said light source along a first path traversing said fluid;
    (c) second light-detecting means so positioned as to detect light traveling from said light source along a second path involving a reflection from the inner wall of said conduit but not traversing said fluid; and
    (d) signal-producing means associated with said first and second light-detecting means and arranged to produce a particular signal when and only when, the levels of light detected separately and simultaneously by said first and second light-detecting means bear a predetermined logical relationship to one another.

5. The detector of claims 1, 3 or 4 in which said conduit is generally circular in cross-section, and said second light-detecting means are positioned along the circumference of said conduit generally midway between said light source and said first light-detecting means.

6. The detector of claims 1, 3 or 4 further comprising:
    (e) clock means arranged to produce a clock pulse whenever a predetermined amount of fluid has been conveyed through said conduit; and
    (f) counting means associated with said first and second logic means and arranged to produce an output when, and only when, said particular signal is continuously present for longer than a predetermined number of clock pulse intervals.

7. The air detector of claim 3 or 4, in which said predetermined logical relationship is that in which the light levels detected by said first and second light-detecting means are substantially different from one another.

8. The air detector of claim 7, in which comparison means are provided for comparing each of said light levels detected by said first and second light-detecting means to a reference level, and said substantial difference exists when, and only when, one of said detected light levels is higher than said reference level, and the other is lower.

9. A method of detecting air in a transparent fluid conduit, the inner wall of the conduit being reflective to light comprising the steps of:
    (a) transmitting light along a first path traversing said fluid, and along a second path involving a reflection from the inner wall of said conduit but not traversing said fluid;
    (b) separately and simultaneously detecting the relative levels of light transmitted through said paths; and
    (c) producing a particular signal representative of whether said light levels are substantially the same or substantially different.

10. The method of claim 9, in which said detected light levels are individually compared to a reference level, and said particular signal is produced when, and only when, one of said light levels is higher than said reference level while the other is lower.

* * * * *